US00PP27879P3

(12) United States Plant Patent
Branhagen

(10) Patent No.: US PP27,879 P3
(45) Date of Patent: Apr. 11, 2017

(54) ***HYDRANGEA* PLANT NAMED 'JOANN'**

(50) Latin Name: *Hydrangea quercifolia*
Varietal Denomination: JoAnn

(71) Applicant: Alan Branhagen, Kingsville, MO (US)

(72) Inventor: Alan Branhagen, Kingsville, MO (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 125 days.

(21) Appl. No.: 14/545,494

(22) Filed: May 12, 2015

(65) Prior Publication Data

US 2016/0338238 P1 Nov. 17, 2016

(51) Int. Cl.
*A01H 5/00* (2006.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Hydrangea* plant named 'JoAnn', characterized by its loosely upright and outwardly spreading plant habit; strong and sturdy stems; relatively small leaves; freely flowering habit; large showy inflorescences with sterile flowers that are initially white in color and with development become pink to rosy violet pink in color; and good garden performance and winter hardiness.

3 Drawing Sheets

Botanical designation: *Hydrangea quercifolia.*
Cultivar denomination: 'JoAnn'.

BACKGROUND OF THE INVENTION

The present invention relates to a new and distinct *Hydrangea* plant, botanically known as *Hydrangea quercifolia* and hereinafter referred to by the name 'JoAnn'.

The new *Hydrangea* plant originated from an open-pollination of an unnamed selection of *Hydrangea quercifolia*, not patented, as the female, or seed parent and an unknown selection of *Hydrangea quercifolia* as the male, or pollen, parent. The new *Hydrangea* plant was discovered and selected by the Inventor as a single flowering plant from within the progeny of the stated open-pollination in a controlled environment in Kingsville, Mo. during the summer of 1999.

Asexual reproduction of the new *Hydrangea* plant by softwood cuttings in a controlled environment in Grand Haven, Mich. since June, 2012 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'JoAnn'. These characteristics in combination distinguish 'JoAnn' as a new and distinct *Hydrangea* plant:

1. Loosely upright and outwardly spreading plant habit.
2. Strong and sturdy stems.

3. Relatively small leaves.
4. Freely flowering habit.
5. Large showy inflorescences with sterile flowers that are initially white in color and with development become pink to rosy violet pink in color.
6. Good garden performance and winter hardiness.

Plants of the new *Hydrangea* differ from plants of the female parent selection in the following characteristics:

1. Plants of the new *Hydrangea* have smaller leaves than plants of the female parent selection.
2. Plants of the new *Hydrangea* are more winter hardy than plants of the female parent selection.

Plants of the new *Hydrangea* can be compared to plants of *Hydrangea quercifolia* 'Ruby Slippers', not patented. In side-by-side comparisons, plants of the new *Hydrangea* differed primarily from plants of 'Ruby Slippers' in the following characteristics:

1. Plants of the new *Hydrangea* were taller than plants of 'Ruby Slippers'.
2. Plants of the new *Hydrangea* and 'Ruby Slippers' differed in developed sterile flower color as plants of 'Ruby Slippers' had ruby red-colored developed sterile flowers.

Plants of the new *Hydrangea* can also be compared to plants of *Hydrangea quercifolia* 'Amethyst', not patented. In side-by-side comparisons, plants of the new *Hydrangea* differed primarily from plants of 'Amethyst' in the following characteristics:

1. Plants of the new *Hydrangea* had longer inflorescences than plants of 'Amethyst'.
2. Plants of the new *Hydrangea* and 'Amethyst' differed in developed sterile flower color as plants of 'Amethyst' had wine red-colored developed sterile flowers.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of typical flowering plants of 'JoAnn' growing in an outdoor nursery.

The photograph on the second sheet is a close-up view of a typical developing inflorescence of 'JoAnn'.

The photograph on the third sheet is a close-up view of a typical developed inflorescence of 'JoAnn'.

Plants used in the photographs were four years old.

DETAILED BOTANICAL DESCRIPTION

Plants used for the following description were grown during the summer in five-gallon containers in a polypropylene-covered shadehouse in Grand Haven, Mich. and under cultural practices typical of commercial *Hydrangea* production. During the production of the plants, day temperatures ranged from 18° C. to 27° C. and night temperatures ranged from 5° C. to 10° C. Plants of the new *Hydrangea* were two years old when the description was taken. Plants were overwintered in a polyethylene-covered greenhouse. In the following description, color references are made to The Royal Horticultural Society Colour Chart, 1995 Edition, except where general terms of ordinary dictionary significance are used.

Botanical description: *Hydrangea quercifolia* 'JoAnn'.

Parentage:

*Female, or seed, parent*.—Unnamed selection of *Hydrangea quercifolia*, not patented.

*Male, or pollen, parent*.—Unknown selection of *Hydrangea quercifolia*, not patented.

Propagation:

*Type cutting*.—By softwood cuttings.

*Time to initiate roots, summer*.—About one month at temperatures about 20° C.

*Time to produce a rooted young plant, summer*.—About three months at temperatures about 20° C.

*Root description*.—Fine to medium in thickness; somewhat fibrous and fleshy; creamy white to brown in color.

*Rooting habit*.—Freely branching; dense.

Plant description:

*Plant form and growth habit*.—Perennial deciduous shrub; loosely upright and outwardly spreading plant habit; broad inverted triangle; strong and sturdy lateral branches; freely branching habit with about eight to ten primary branches developing per plant; vigorous growth habit and rapid growth rate.

*Plant height*.—About 80 cm to 110 cm.

*Plant diameter or area of spread*.—About 86 cm.

*Lateral branches*.—Length: About 54 cm. Diameter: About 1 cm. Internode length: Distally, about 4 cm to 6 cm; proximally, about 11.5 cm. Strength: Strong, sturdy. Aspect: About 5° to 50° from vertical. Texture: Developing branches are pubescent and become woody with development, mature bark exfoliating. Color, developing: Close to 145C; pubescence, close to 164A. Color, developed: Close to between 200B to almost 199B.

Leaf description:

*Arrangement*.—Opposite, simple.

*Length*.—About 11 cm to 19 cm.

*Width*.—About 9 cm to 14 cm.

*Shape*.—Pinnately-lobed.

*Apex*.—Cuspidate.

*Base*.—Obtuse.

*Margin*.—Serrulate.

*Texture, upper surface*.—Smooth, glabrous; slightly rigid.

*Texture, lower surface*.—Rough, pubescent; rigid.

*Venation pattern*.—Pinnate.

*Color*.—Developing leaves, upper surface: Close to 138B. Developing leaves, lower surface: Close to 145D. Fully expanded leaves, upper surface: Close to 137A; venation, close to 143C. Fully expanded leaves, lower surface: Close to 138B; venation, close to 145C.

*Petioles*.—Length: About 3 cm to 6 cm. Diameter: About 5 mm. Texture, upper and lower surfaces: Smooth, velvety. Color, upper surface: Close to 145C and 164A. Color, lower surface: Close to 145C.

Inflorescence & flower description:

*Flower type and habit*.—Single sterile and fertile flowers arranged on large terminal panicles; flowers face upright and outwardly.

*Fragrance*.—Very faint; sweet.

*Natural flowering season*.—Continuous flowering from mid to late summer in Grand Haven, Mich.

*Quantity of flowers*.—Freely flowering habit; about 1,300 fertile flowers and about 58 sterile flowers develop per inflorescence.

*Inflorescence height*.—About 19 cm to 36 cm.

*Inflorescence diameter*.—About 9 cm to 18 cm.

*Flower diameter, fertile flowers*.—About 6 mm.

*Flower depth (height), fertile flowers*.—About 3 mm.

*Flower diameter, sterile flowers*.—About 3 cm to 4 cm.

*Flower depth (height), sterile flowers*.—About 1.5 cm.

*Flower buds, fertile and sterile flowers*.—Length: About 3 mm. Diameter: About 3 mm. Shape: Clavate. Color: Close to 195C.

*Petals, fertile flowers*.—Arrangement: Five in a single whorl. Length: About 3 mm. Width: About 2 mm. Shape: Ovate. Apex: Acute. Base: Acute. Margin: Entire. Texture, upper and lower surfaces: Smooth, glabrous. Color: When opening, upper and lower surfaces: Close to 145D. Fully opened, upper and lower surfaces: Close to 145D; color does not change with development.

*Petals, sterile flowers*.—Arrangement: Four in a single whorl. Length: About 2 mm. Width: About 1 mm. Shape: Ovate. Apex: Obtuse. Base: Obtuse. Margin: Entire. Texture, upper and lower surfaces: Smooth, glabrous. Color: When opening, upper and lower surfaces: Close to 155A. Fully opened, upper and lower surfaces: Close to 155A; color does not change with development.

*Sepals, fertile flowers*.—Quantity per flower: Five in a single whorl. Length: About 3 mm. Width: About 2 mm. Shape: Ovate. Apex: Acute. Base: Acute. Margin: Entire. Texture, upper and lower surfaces: Smooth, glabrous. Color: When opening, upper and lower surfaces: Close to 145D. Fully opened, upper and lower surfaces: Close to 145D; color does not change with development.

*Sepals, sterile flowers*.—Quantity per flower: Four in a single whorl. Length: About 1.5 cm to 2 cm. Width: About 1.7 cm to 2.3 cm. Shape: Obovate. Apex: Obtuse. Base: Obtuse. Margin: Entire. Texture, upper and lower surfaces: Smooth, glabrous. Color: When opening, upper and lower surfaces: Close to 155A. Fully opened, upper and lower surfaces: Close to 155A; with development, color becoming closer to 186B and then becoming closer to 63A.

*Pedicels, fertile flowers*.—Length: About 1.5 mm. Diameter: Less than 1 mm. Strength: Strong. Angle: Erect to about 90° from inflorescence axis. Texture: Smooth, glabrous. Color: Close to 145B.

*Pedicels, sterile flowers*.—Length: About 1.1 cm to 1.6 cm. Diameter: About 1 mm. Strength: Strong, sturdy. Angle: About 5° to about 45° from inflorescence axis. Texture: Smooth, glabrous. Color: Close to 145B.

*Reproductive organs, fertile flowers*.—Stamens: Quantity per flower: About ten. Filament length: About 6 mm. Filament color: Close to 155A. Anther shape: Round. Anther length: About 1 mm. Anther color: Close to 3D. Pollen amount: Moderate. Pollen color: Close to 3D. Pistils: Pistil quantity per flower: Two or three. Pistil length: Less than 0.5 mm. Stigma shape: Oblong. Stigma color: Close to 145D. Style length: Less than 0.5 mm. Style color: Close to 145D. Ovary color: Close to 146D.

*Reproductive organs, sterile flowers*.—Stamens: Quantity per flower: About eight. Filament length: About 3 mm. Filament color: Close to 155A. Anther shape: Lobed. Anther length: About 0.5 mm. Anther color: Close to 155A. Pollen amount: Moderate. Pollen color: Close to 18A. Pistils: Pistil quantity per flower: One. Pistil length: About 0.5 mm. Stigma shape: Two to three-lobed. Stigma color: Close to 155A. Style length: About 0.5 mm. Style color: Close to 155A. Ovary color: Close to 155A and 145C.

*Seeds and fruits*.—Seed and fruit development has not been observed on plants of the new *Hydrangea*.

Disease & pest resistance: Plants of the new *Hydrangea* have not been observed to be resistant to pathogens and pests common to *Hydrangea* plants.

Garden performance: Plants of the new *Hydrangea* have been observed to have good garden performance by exhibiting good tolerance to rain and wind. In addition, plants of the new *Hydrangea* have been observed to have good winter hardiness and high temperature tolerance as plants have been observed to tolerate temperatures ranging from about −29° C. to about 40° C.

It is claimed:

1. A new and distinct *Hydrangea* plant named 'JoAnn' as illustrated and described.

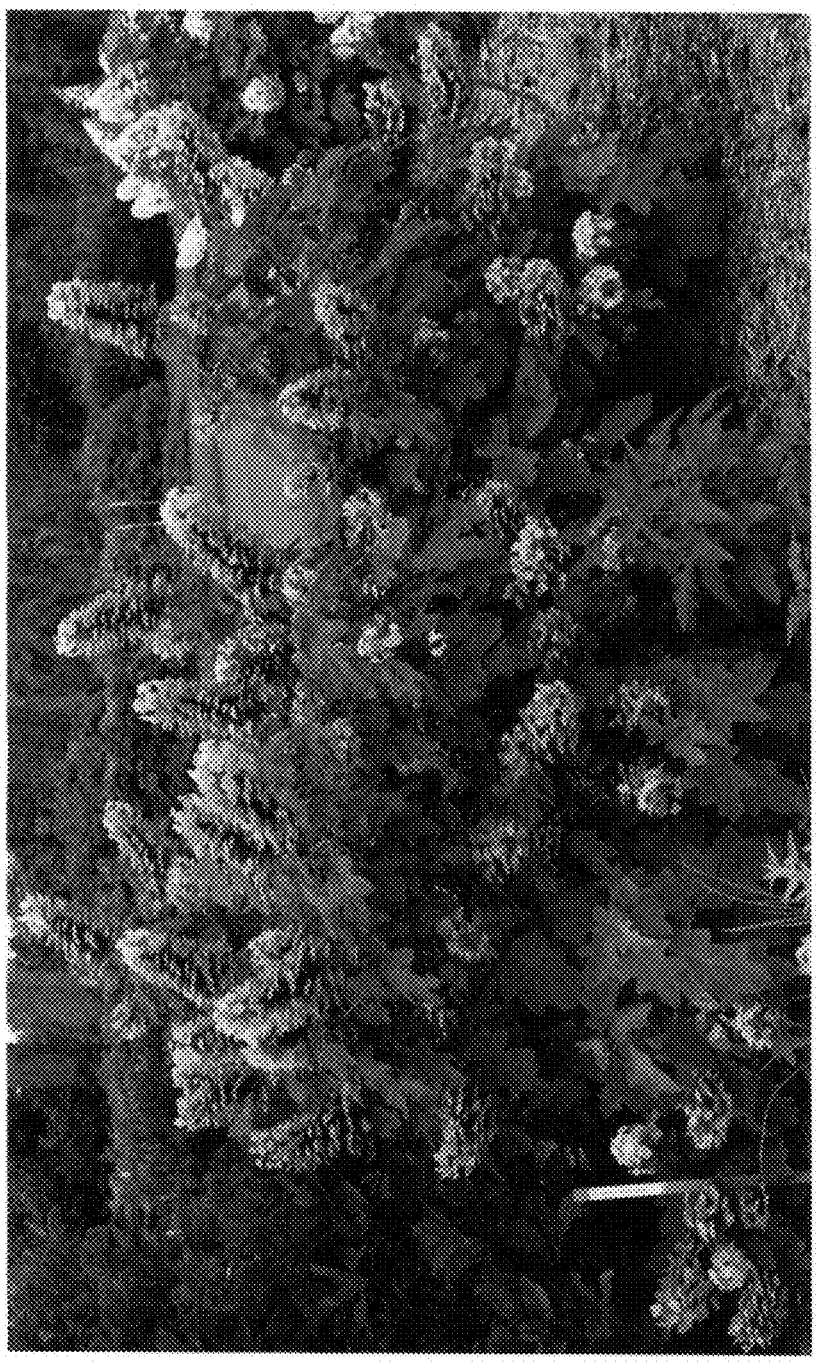

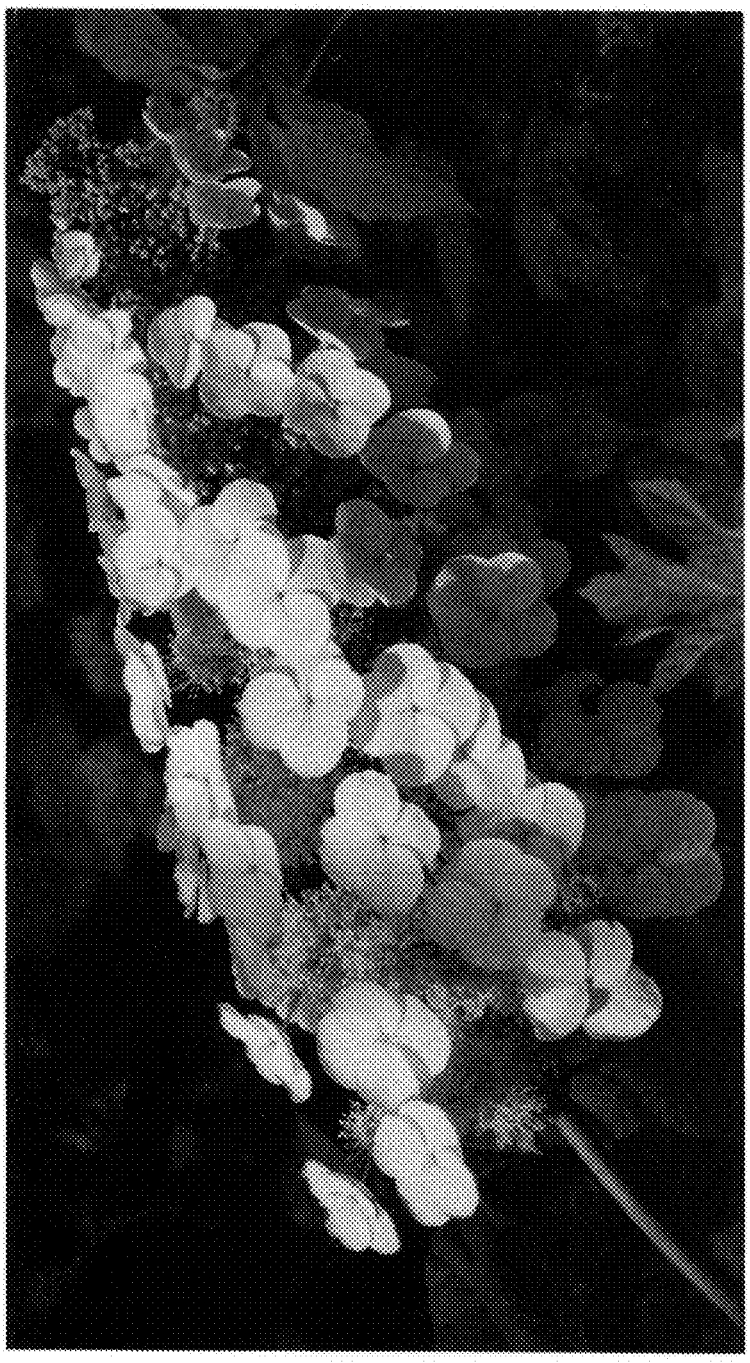

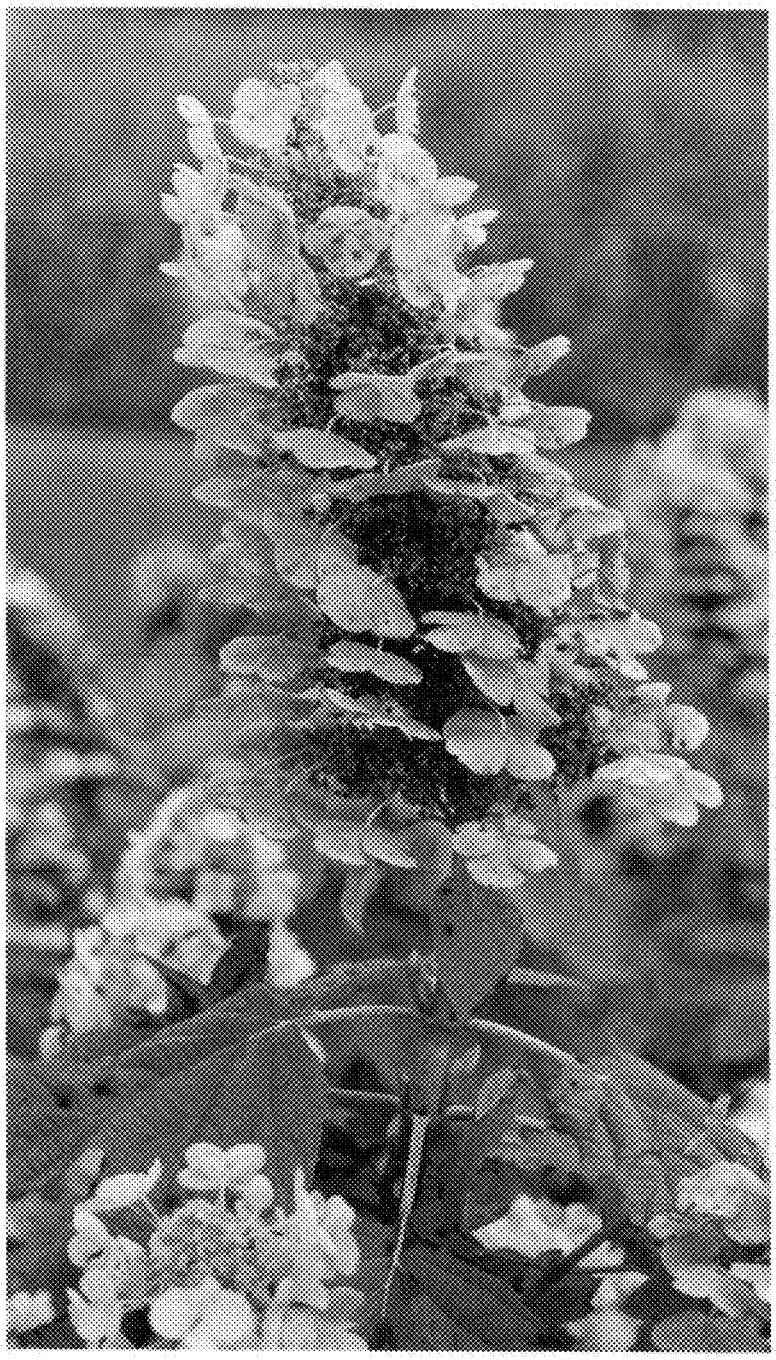

* * * * *